United States Patent
Peters et al.

(10) Patent No.: US 10,987,514 B2
(45) Date of Patent: Apr. 27, 2021

(54) SYSTEM AND METHOD FOR MINIMALLY INVASIVE LEAD IMPLANTATION FOR CAVERNOSAL NERVE STIMULATION CONTROLLED AND POWERED WIRELESSLY FROM AN EXTERNAL SOURCE

(71) Applicants: Kenneth M. Peters, Huntington Woods, MI (US); Larry T. Sirls, Bloomfield Hills, MI (US)

(72) Inventors: Kenneth M. Peters, Huntington Woods, MI (US); Larry T. Sirls, Bloomfield Hills, MI (US)

(*) Notice: Subject to any disclaimer, the term of this patent is extended or adjusted under 35 U.S.C. 154(b) by 715 days.

(21) Appl. No.: 15/647,155

(22) Filed: Jul. 11, 2017

(65) Prior Publication Data

US 2018/0015288 A1 Jan. 18, 2018

Related U.S. Application Data

(60) Provisional application No. 62/362,976, filed on Jul. 15, 2016.

(51) Int. Cl.
*A61N 1/36* (2006.01)
*A61N 1/05* (2006.01)
(Continued)

(52) U.S. Cl.
CPC ............ *A61N 1/36107* (2013.01); *A61F 5/41* (2013.01); *A61N 1/0521* (2013.01); *A61N 1/0551* (2013.01); *A61N 1/36007* (2013.01); *A61N 1/3787* (2013.01); *A61N 1/37247* (2013.01); *A61F 2005/414* (2013.01); *A61F 2005/418* (2013.01)

(58) Field of Classification Search
CPC .... A61N 1/00; A61N 1/36007; A61B 5/4393; A61B 5/0031; A61B 5/00; A61B 5/026; A61B 8/06; A61B 8/4227; A61B 5/0022; A61B 8/488; A61B 5/1107; A61B 5/0053; A61B 5/1072; A61B 5/1121; A61B 5/14551; A61B 5/01; A61B 8/485
See application file for complete search history.

(56) References Cited

U.S. PATENT DOCUMENTS 2,581,114 A 1/1952 Larson
2,818,855 A 1/1958 Miller
(Continued)

*Primary Examiner* — Jon Eric C Morales
(74) *Attorney, Agent, or Firm* — Daniel W. Roberts; Law Offices of Daniel W. Roberts, LLC

(57) ABSTRACT

Provided is a system and method for cavernosal neuromodulation as directed by a wireless remote controller and power supply. The system including: an implantable lead having at least one electrode structured and arranged to be disposed proximate to the cavernous nerve in a penis; a portable power supply; and a controller having wireless communication electronics and control circuitry associated with the wireless communication electronics structured and arranged to wirelessly couple the power supply to the at least one electrode, the controller further structured and arranged to permit a user to select at least one instruction set for the at least electrode. The controller and power supply may be provided by a control ring. An associated method of use is also provided.

19 Claims, 13 Drawing Sheets

(51) Int. Cl.
    *A61N 1/372*      (2006.01)
    *A61N 1/378*      (2006.01)
    *A61F 5/41*      (2006.01)

(56) References Cited

U.S. PATENT DOCUMENTS

| | | |
|---|---|---|
| 3,511,230 A | 5/1970 | Strong |
| 3,612,047 A | 10/1971 | Nesbit |
| 3,636,948 A | 1/1972 | Atchley |
| 3,759,253 A | 9/1973 | Cray |
| 3,794,020 A | 2/1974 | Bagby |
| 4,203,432 A | 5/1980 | Koch |
| 5,336,157 A | 8/1994 | Hale |
| 5,628,329 A | 5/1997 | Bennett et al. |
| 5,873,813 A | 2/1999 | Weiss |
| 5,938,584 A | 8/1999 | Ardito et al. |
| 6,926,666 B2 | 8/2005 | Magee |
| 7,899,539 B2 | 3/2011 | Whitehurst et al. |
| 9,199,087 B2 | 12/2015 | Perryman et al. |
| 9,220,897 B2 | 12/2015 | Perryman et al. |
| 9,409,030 B2 | 8/2016 | Perryman et al. |
| 9,566,449 B2 | 2/2017 | Perryman et al. |
| 2006/0247682 A1* | 11/2006 | Gerber .............. A61N 1/36007 607/2 |
| 2007/0255333 A1 | 11/2007 | Giftakis et al. |
| 2008/0183236 A1 | 7/2008 | Gerber |
| 2011/0152877 A1 | 6/2011 | Bly |
| 2014/0171767 A1* | 6/2014 | Hotaling .............. A61B 5/4393 600/323 |
| 2015/0352357 A1* | 12/2015 | Wei .................... A61N 1/36031 604/385.03 |

\* cited by examiner

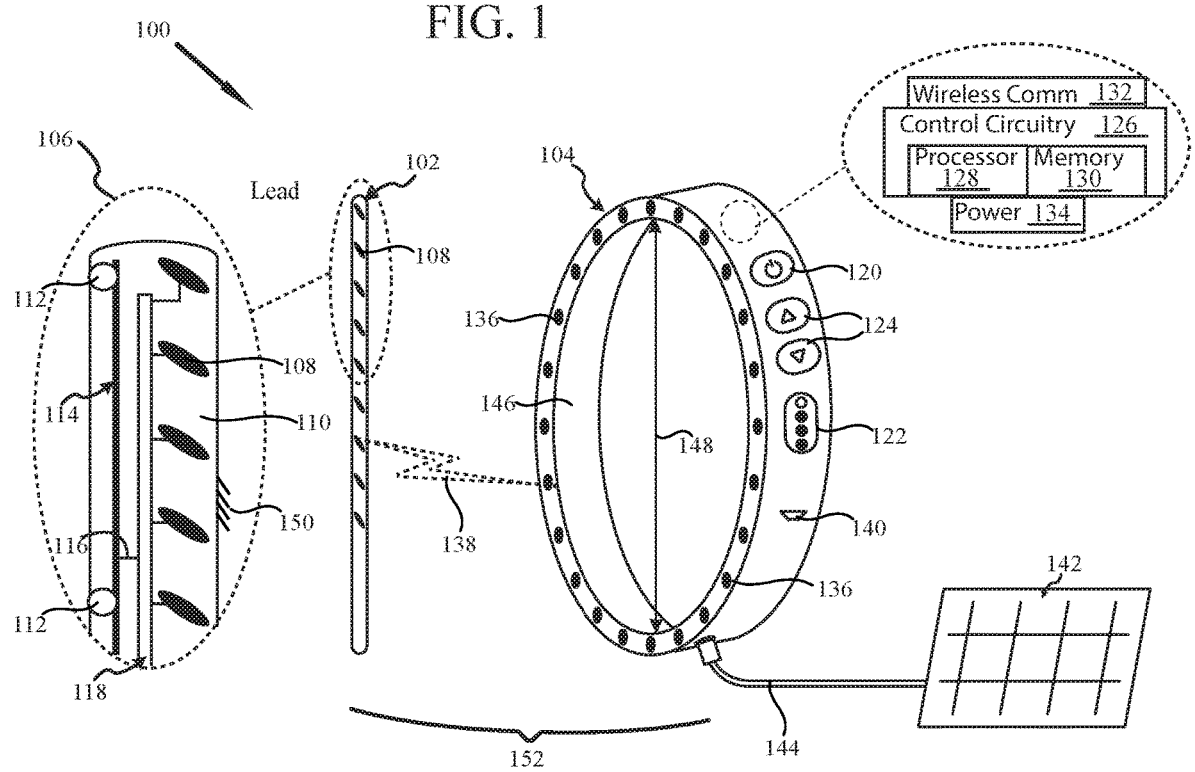
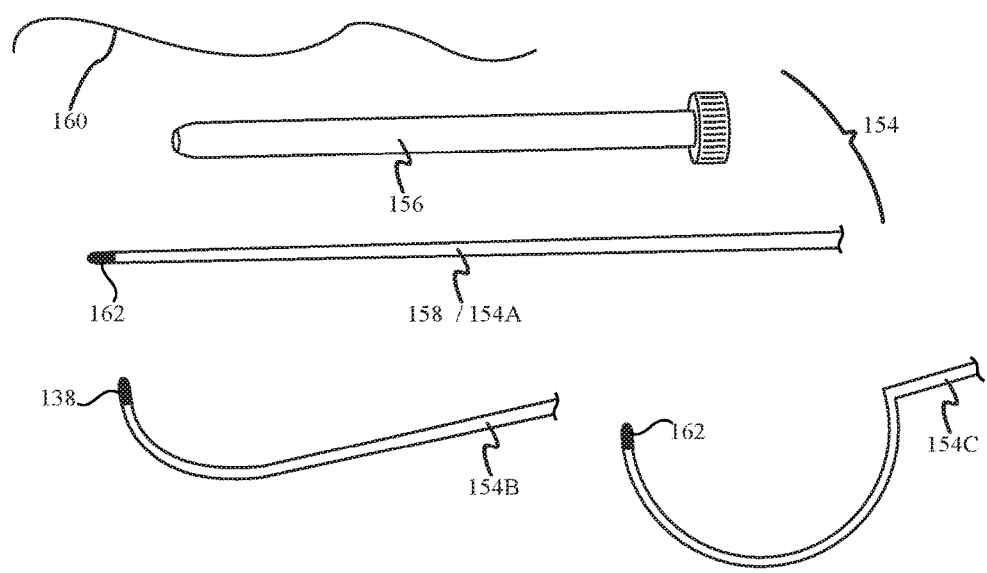
FIG. 1

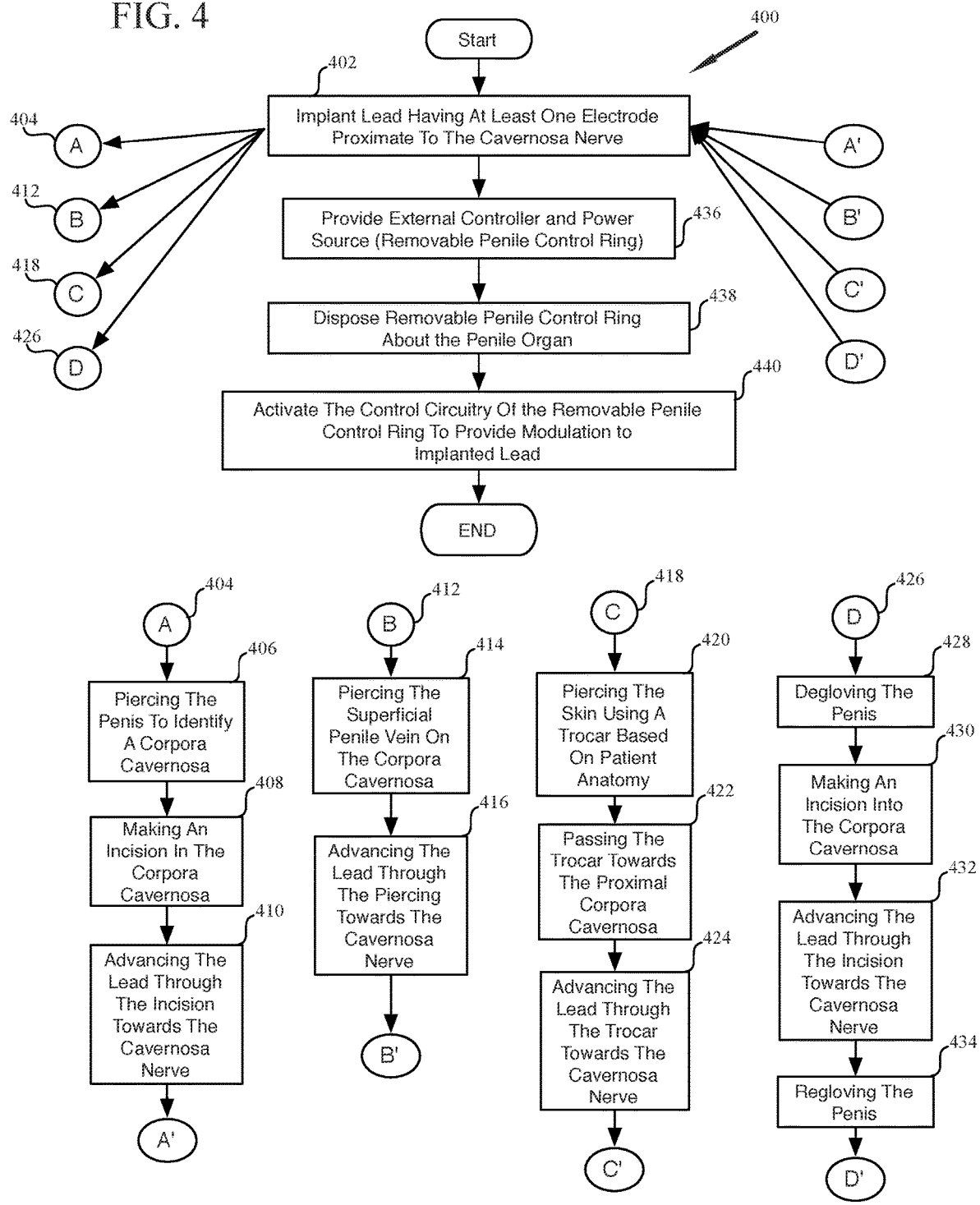

INTRAVENOUS LEAD PLACEMENT

INTRACAVERNOSAL LEAD PLACEMENT

RETROPUBIC LEAD PLACEMENT

INFRAPUBIC LEAD PLACEMENT

TRANS OBTURATOR LEAD PLACEMENT

SYSTEM AND METHOD FOR MINIMALLY INVASIVE LEAD IMPLANTATION FOR CAVERNOSAL NERVE STIMULATION CONTROLLED AND POWERED WIRELESSLY FROM AN EXTERNAL SOURCE

CROSS REFERENCE TO RELATED APPLICATIONS

This application claims the benefit under 35 U.S.C. § 119(e) of U.S. Provisional Application No. 62/362,976 filed Jul. 15, 2016 and entitled SYSTEM AND METHOD FOR CAVERNOSAL NERVE STIMULATION, the disclosure of which is incorporated herein by reference.

FIELD OF THE INVENTION

The present invention relates generally to a system to stimulate the cavernosal nerve(s) using either an intra penile or extra penile approach to provide a penile erection. The system includes instruments and techniques to place a lead in proximity to the cavernous nerve, and use of a compressive penile ring that serves as an external power source and controller unit.

BACKGROUND

The male penis includes a pair of corpora cavernosa located laterally within the penis, a pair of penile arteries situated deep within their respective corpora cavernosa, dorsal penile veins and a neurovascular bundle located along an upper midline proportion of the penis, a corpus spongiosum located along a lower portion of the penis, a urethra located within the corpus spongiosum, and stretchable tunica and skin.

Generally, in the male penis, an erection is produced when the cavernosal nerves stimulate an increase in arterial blood flow into the spongy, cavernosal tissues of the penis. The increase in blood flow increases the pressure in the penis and is critical in the generation of a rigid, erect penis.

Modulation or stimulation of the cavernous nerve by electrical stimulation is an important target for clinical therapy for men who suffer from erectile dysfunction from a variety of causes. At the present time, the options for stimulation of the cavernosal nerves are extremely limited. In addition, traditional implanted leads for nerve stimulation require an implantable power source with direct-wired connection to the stimulation lead.

Previously described approaches to place a lead for chronic electrical stimulation of the cavernous nerve have limitations in that they required an operating room and anesthesia to allow an open surgical incision and exposure of the nerve with cuff placement around the nerve to prevent lead migration and maximize nerve activity.

In addition, as noted above, the traditional implantation methodologies require that the stimulating electrode needs to be connected to an implantable power source (pulse generator) that is powered by a fixed or rechargeable energy source that is directly connected to the leads. This requires a larger incision, or a second incision to implant the energy source. There are limited anatomic locations in proximity to the penis that allow implantation of an energy source that would not interfere with physical sexual activity.

Prior successful cavernosal nerve stimulation resulting in penile erection was reported in a dog model by Shafik in 1995. He published a report of an open surgical approach, with an incision above and lateral to the penis and under the pubic bone to place a lead that was wrapped around the cavernous nerve. Wrapping the lead around the nerve was to try and minimize lead migration and loss of clinical effect. Stimulation of this lead resulted in increasing intracavernosal pressure (showing increased blood flow into the penis) and full erection.

Previous patents involving penile nerve stimulation, such as U.S. Pat. No. 5,938,584 to Ardito et al, U.S. Pat. No. 7,899,539 to Whitehurst et al., US Pub 2008/0183236 to Gerber, and US Pub 2007/055333 to Giftakis et al., have focused on an open surgical dissection to locate the cavernous nerve and place an electrode along the cavernous nerve proximal to the insertion into the corpora cavernosa of the penis. In the human, the neurovascular bundle travels along the lateral aspect of the prostate bilaterally and at the apex of the prostate, near the urethral junction the cavernous nerve becomes a single or branched nerve.

The cavernous nerve travels in front of the pubic bone and inserts into the tunica albuginea of the anterior and proximal aspect for the corpora cavernosa bilaterally. The nerve then branches into many small nervelets and develops a diffuse plexus of nerves in the corpora cavernosa that invest the penis shaft, from the pubic bones to the head of the penis, where they join. These formations are made of a sponge-like tissue containing irregular blood-filled spaces lined by endothelium and separated by connective tissue septum. It is the corpora cavernosum that engorge with blood during an erection compressing the venous outflow resulting in penis lengthening and rigidity.

In the human model, this open surgical approach requires the surgeon to cut the suspensory ligament of the penis to gain access to the cavernous nerve (the suspensory ligament allows the engorged penis to stand erect and stable allowing vaginal penetration, when the ligament is cut the penis can be engorged and erect but will not be stable). Alternative open surgical approaches would be even more invasive by approaching the nerve from the perineum, or through the abdomen, both relatively morbid surgery with associated risks, requiring anesthesia and an operating room.

The open surgical approach of the above references also requires placement of an implantable pulse generator that was powered by either a fixed or rechargeable energy source and controlled remotely. The direct wire connection of the energy source to the lead requires further surgical dissection in order to attach it to the lead at the nerve.

These limitations have made it difficult for industry to develop a successful neuromodulation implant to stimulate the cavernosal nerve. No previous patents around cavernous nerve stimulation have resulted in development of a commercially available product.

A second component important in the generation and maintenance of an erect penis is the compression of the superficial veins of the penis. The superficial venous system drains the blood from the penis. Because the veins draining blood from the penis are superficial, and the arteries delivering blood to the penis are deeper inside the penis, a current clinical technique used to enhance penile erection is to place a compressive band around the base of the erect penis that compresses these superficial veins.

Venous leak is well known to contribute to poor erection quality and duration (Wespes et al, J Urology [1985, 133 (5):796-798], and constricting penile rings have been used clinically for decades (see, U.S. Pat. No. 5,873,813 to Weiss entitled Method And Apparatus For Producing And Maintaining A Penile Erection, U.S. Pat. No. 5,336,157 to Hale entitled Penile Clamp For Impotence). With compression of the penile veins, drainage of blood from the engorged penis is restricted, yet the deeper arterial inflow continues, so that the erectile tissues become further engorged with blood, and the penis more rigid.

Moreover, an erection is produced when the cavernosal nerves stimulate increase in arterial blood flow into the spongy, cavernosal tissues of the penis, combined with compression of venous return with penile blood outflow restricted so that the erectile tissues become filled or engorged with blood.

Thus, cavernosal nerve stimulation to turn on arterial blood in flow is augmented by superficial venous compression that helps to trap the blood in the cavernosal tissues and increase pressure in the cavernosal bodies causing penile rigidity, yet existing medical procedures and devices fall short of addressing both issues.

Vacuum erection devices, for example, achieve an erection by improving blood to flow into the penis through suction. The vacuum, however, must be removed for coitus, and thus, the erection can be lost.

Hence there is a need for a method and system that is capable of overcoming one or more of the above identified challenges.

SUMMARY OF THE INVENTION

Our invention solves the problems of the prior art by providing novel systems and methods for minimally invasive injectable intra penile or trocar based percutaneous placement of a nerve stimulation lead to stimulate the cavernous nerve and control via an external penile ring worn at the base of the penis.

In particular, and by way of example only, according to one embodiment of the present invention, provided is a system for cavernosal neuromodulation controlled and powered wirelessly from an external source, comprising, including: an implantable lead having at least one electrode structured and arranged to be disposed proximate to the cavernous nerve in a penis; a portable power supply; and a controller having wireless communication electronics and control circuitry associated with the wireless communication electronics structured and arranged to wirelessly couple the power supply to the at least one electrode, the controller further structured and arranged to permit a user to select at least one instruction set for the at least one electrode.

In yet another embodiment, provided is a kit for cavernosal neuromodulation controlled and powered wirelessly from an external source, comprising, including: a removable penile control ring having a flexible body formed of a resilient material enclosing: wireless communication electronics; a power supply; and control circuitry associated with the wireless communication electronics and power supply; and an implantable lead having at least one electrode structured and arranged to be disposed proximate to the cavernous nerve in a penis, the implantable lead having at least one electrode having wireless communication electronics adapted to receive power and control from the penile control ring.

For yet another embodiment, provided is a method for cavernosal neuromodulation controlled and powered wirelessly from an external source, comprising, including: implanting at least one implantable lead having at least one electrode proximate to the cavernous nerve in a penis; providing a power supply and a controller having wireless communication electronics and control circuitry associated with the wireless communication electronics structured and arranged to wirelessly couple the power supply to the at least one electrode, the controller further structured and arranged to permit a user to select at least one instruction set for the electrode; activating the controller to provide at least one selected instruction set to the at least one implantable lead having the at least one electrode, thereby stimulating the cavernous nerve.

Yet for another embodiment, provided is a method for cavernosal neuromodulation controlled and powered wirelessly from an external source, comprising, including: implanting at least one implantable lead having at least one electrode proximate to the cavernous nerve in a penis, the at least one implantable lead having the at least one electrode having wireless communication electronics adapted to receive power and control from an external controller; providing as an external controller a removable penile control ring having a flexible body formed of a resilient material enclosing: wireless communication electronics; a power supply; and control circuitry associated with the wireless communication electronics and power supply; disposing the removable penile control ring about the penis; and activating the control circuitry of the removable penile control ring to provide at least one selected instruction set to the at least one implantable lead having the at least one electrode, thereby stimulating the cavernous nerve.

BRIEF DESCRIPTION OF THE DRAWINGS

FIG. 1 is a conceptual view of the implantable lead and controlling penile ring as may be provided as a kit and optional medical tools to assist with the implant procedure, in accordance with at least one embodiment of the present invention;

FIG. 4 is a high-level flow chart of at least one method for cavernous nerves stimulation with an external power supply and controller in accordance with at least one embodiment of the present invention;

DETAILED DESCRIPTION

Figure 2:
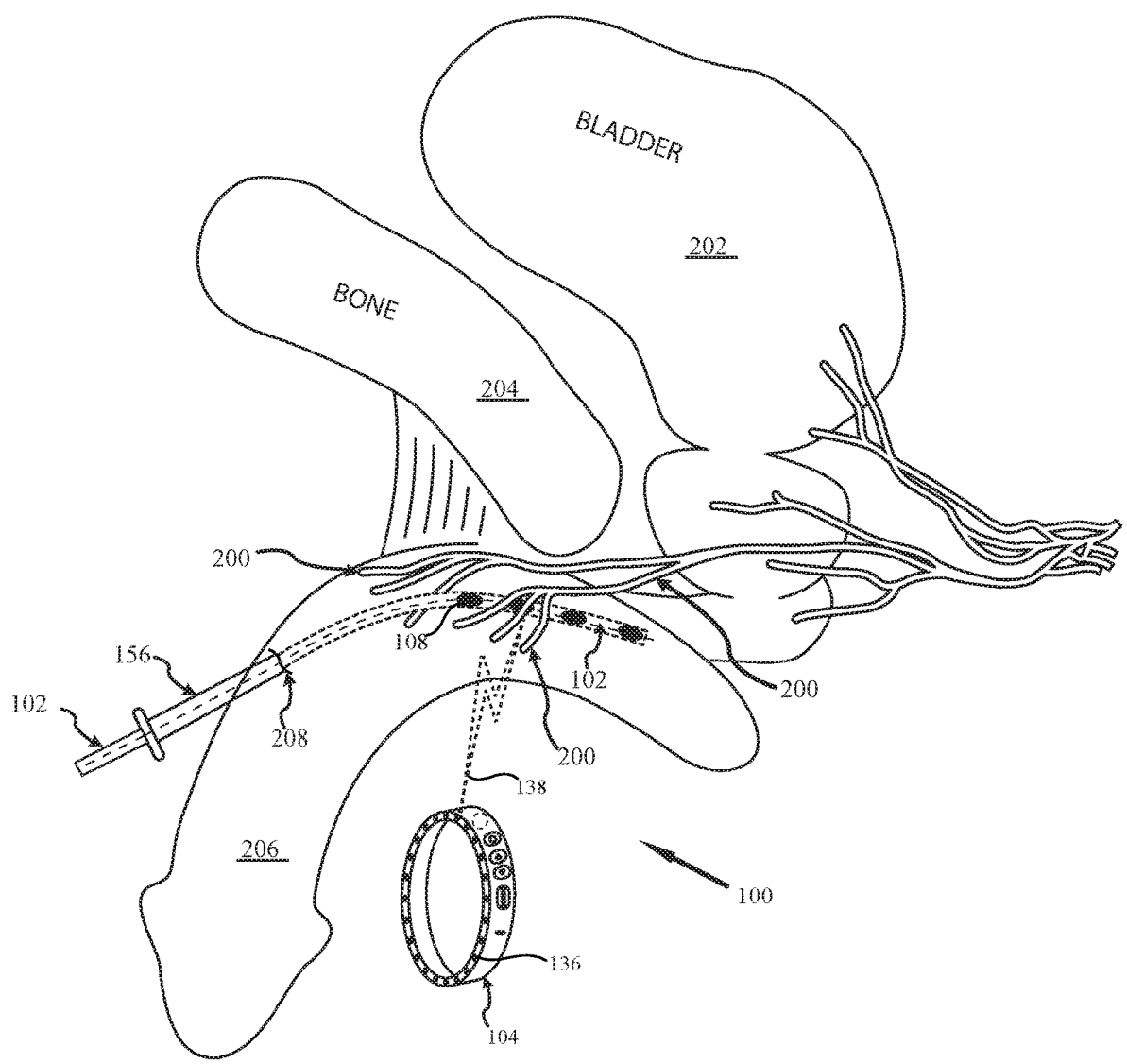
FIG. 2 is a general cross view of the implantable lead and penile ring system showing the corpora cavernosal lead introducer, appropriate for patients anatomy, and the lead placed proximate to the cavernous nerve, in accordance with at least one embodiment of the present invention.

Before proceeding with the detailed description, it is to be appreciated that the present teaching is by way of example only, not by limitation. The concepts herein are not limited to use or application with a specific system or method for intra penile or extra penile cavernous nerve stimulation with external penile ring controller. Thus, although the instrumentalities described herein are for the convenience of explanation shown and described with respect to exemplary embodiments, it will be understood and appreciated that the principles herein may be applied equally in other types of systems and methods involving cavernous nerve stimulation.

This invention is described with respect to preferred embodiments in the following description with reference to the Figures, in which like numbers represent the same or similar elements. Further, with the respect to the numbering of the same or similar elements, it will be appreciated that the leading values identify the Figure in which the element is first identified and described, e.g., element 100 first appears in FIG. 1.

Turning now to the Figures, and more specifically to FIG. 1 there is shown a Cavernosal Lead and Ring System (hereinafter CLRS 100) for the controlled stimulation of the cavernous nerve, e.g. neuromodulation of the cavernous nerve, and penile venous leak compression, in accordance with at least one embodiment of the present invention. Neuromodulation is typically defined and understood to be the alternation of nerve activity through targeted delivery of a stimulus, such as by electrical stimulation to specific neurological sites in the body. Moreover, different electrical stimulation, such as current and waveform may induce different nerve activity and/or intensity of nerve activity.

As shown, the CLRS 100 is provided by two key components, an implantable lead 102 and control ring 104. As physically separate, but interactive components, the implantable lead 102 and control ring 104 are highly advantageous.

The implantable lead's 102 primary role is to dispose one or more electrodes adjacent to the cavernous nerve—a discreet role in that there is no additional power supply or separate control system that is also implanted. The control ring's 104 primary role is as power generator, antenna and controller of the nerve stimulation achieved by the electrodes of the implantable lead 102. This interaction between the implantable lead 102 and the control ring 104 is achieved, at least in party by electrical radiative coupling. Moreover, only the lead 102 is implanted in the patient.

There are two main types of electrical radiative coupling, capacitive coupling and inductive coupling. Capacitive coupling is the transfer of energy between components by means of a displacement current induced by electrical fields triggered by electrodes and is generally functional within 1-2 centimeters. Inductive coupling relies on magnetic fields and is generally functional within 1 centimeter to 1 meter. For purposes of varying embodiments of CLRS 100, the selection of capacitive, inductive or even both will be a matter of fabrication and design choice at the time of fabrication.

As shown more clearly in the enlarged section 106, lead 102 is an implantable neural stimulator containing at least one, and more commonly a plurality, of electrodes 108 in an electrically insulating material 110. A plurality of antenna coupling contacts 112 are also provided about the lead 102 and are electrically coupled to antenna 114 by electrical wires not shown in FIG. 1. For at least one embodiment, the antenna 114 is a dipole antenna. The length and number of antennas 114 and antenna coupling contacts 112 may vary, but is generally understood to be pre-selected for viable receipt by the lead 102 of energy provided by at least one external antenna through electrical radiative coupling.

The antenna 114 is in turn coupled by wires 116 to waveform conditioning circuitry 118, which may include electrical components, such as but not specifically limited to, resistors, capacitors, diodes, isolation circuitry, charge balance microelectronics to prevent corrosion of the electrodes 108, and or other components.

The waveform conditioning circuitry 118 can use the incoming energy receive by the antenna 114 through the antenna coupling contacts 112 to provide a stimulation waveform to the electrodes 108 for the excitation of the cavernous nerves. For at least one embodiment, frequencies from about 800 MHz to about 5.8 GHz may be received by the antenna 114. The waveform conditioning circuitry 118 rectifies this energy to provide wave forms at lower frequencies, e.g., about 5 Hz to about 1000 Hz.

It is to be specifically understood and appreciated that as shown and described thus far, lead 102 is not directly wired to either a remote power supply located elsewhere within the body, or directly wired to a controller whether internal or external. As will be appreciated from the following description and accompanying illustrations, the lead 102 is controlled and powered wirelessly from a remote controller. Although this remote controller may be an application for a smartphone device, or as a separate device that is held in a pocket, on a neckless, or placed nearby, for at least one embodiment the controller is provided as a specific device aiding user overcoming erectile dysfunction—a compressive penis ring.

Moreover, for at least one embodiment as shown in FIG. 1, and adjacent to the lead 102, is a control ring 104, which is intended to be placed over the \penis and proximate to the base of the penis when desired for use. As conceptually illustrated, for at least one embodiment, the control ring 104 has a power button 120, a status indicator 122, one or more controls 124, such as for different instruction sets (e.g. programs) to direct the waveform conditioning circuitry 118 of the lead 102 to engage the electrodes 108 for neuromodulation/stimulation of cavernous nerve stimulation.

Control ring 104 further includes a control circuitry 126, typically including a processor 128 and non-volatile memory 130, wireless communication electronics 132, a power supply 134 and at least one antenna 136. The at least one antenna 136 may be composite structure or a plurality of distinct structures that are operable to provide both control signals and electrical radiative coupling with the lead 102. For at least one embodiment, at least a portion of the antennas 136 are dipole antennas. The wireless communication electronics 132 are electrically coupled to the one or more antennas 136 embedded within control ring 104.

The control circuitry 126, and more specifically the non-volatile memory 130 has executable instructions to direct the operation of the processor 128 to control the wireless communication electronics 132 to transmit via the at least one antenna 136 an output signal 138 containing electrical energy to be received by the lead 102 by radiative coupling.

More specifically, the output signal 138 provided by the at least one antenna 136 may be selected from the range of frequencies from about 800 MHz to about 5.8 GHz. The control circuitry 126 in response to user directives may direct a substantially sustained output signal 138, or modulate the output signal 138 as both intensity, pulse, frequency and/or combinations thereof. As the control ring 104 is disponed about the base of the penis, the control ring 104 is also very likely advantageously proximate to the implanted lead 102.

For at least one embodiment, the power supply 134 is a battery and is rechargeable, and may be recharged by induction from an external source, or by direct connection, such as through a port 140, e.g. a USB port, provided in the exterior of control ring 104. Port 140 may also be used to provide new instructions to the non-volatile memory 130.

For at least one embodiment, the wireless communication component is also structured and arranged such that the control ring 104 may be operated by an application provided to a smart phone or other remote computing device connected by Bluetooth, ad-hoc, or other wireless network technology to the control ring 104.

As is also shown, for at least one optional embodiment, the control ring 104 may be coupled to an external antenna 142, such as by flexible wiring 144 and port 140. External antenna may be provided as a flexible adhesive patch that may be applied temporarily to the skin. For yet another optional embodiment, the external antenna may be incorporated as part of a garment, such as underwear.

For at least one embodiment the body of the control ring 104 is substantially formed of a resilient material such as rubber, silicone or other appropriate material. More specifically, for at least one embodiment at least the body of the control ring 104 is formed of medical grade silicone. The inner circumferential surface 146 is intended to be in direct contact with the skin of the penis, and therefore may be made supple. Varying embodiments may further include an inner circumferential spring, and or an adjustor disposed within the control ring 104 to permit user adjustment of the minimum interior diameter 148 of the control ring 104.

Moreover, the control ring 104 may be a circumferential stretching band, open or closed, stretching or fixed size, and can be band, ring, or clamp shaped (U.S. Pat. Nos. 2,581,114, 2,818,855, 3,511,230, 3,612,047, 3,636,948, 3,759,253, 3,794,020, and 4,203,432 are examples of these constrictive devices), and devices such as these may serve as an off-the-shelf component to be augmented under the present invention through the addition of the components as noted above so as to provide control ring 104.

Collectively, the lead 102 and the control ring 104 provide the advantageous CLRS 100. The antennas 136 of the control ring 104 are physically separate from the antennas 114 of the lead 102 and the neural stimulator electrodes 108, yet, the output signal 138 provided by the control ring 104 is received by the lead 102 and processed by the waveform conditioning circuitry 118 so as to induce the electrodes to stimulate the cavernous nerves when desired. And, as a constrictive penile ring, the control ring 104 further provides an external compressive force about the base of the penis so as to further assist in maintaining an erection as induced by the stimulation of the cavernous nerves by the lead 102.

To briefly summarize, the implantable lead 102 having at least one electrode 108 may be considered an implantable wireless neural stimulator having components to receive radio frequency, "RF" transmission signals and at least one electrode 108 to deliver stimulation to neural tissue of the cavernous nerves via electrical radiative coupling.

Moreover, the components of the implantable lead 102 as a neural stimulator are structured and arranged to capture energy transmitted by the external power source and controller, i.e. the control ring 104, and convert this energy into an electrical waveform. The implantable lead 102, and more specifically the waveform conditioning circuitry 118, further modifies this waveform to create an electrical pulse to be applied by the one or more electrode 108 to the neural tissue of the cavernous nerves, thus providing neuromodulation of the cavernous nerves 200.

During the implant procedure for the lead 102, the practitioner or clinician may test the neuromodulation of the cavernous nerves 200 to determine the optimum current and waveform for the current patient. This information may then be encoded as part of the instructions in the non-volatile memory 130. Further variables of rate (Hz), pulse width (usec), current (milliamps), interval (continuous or cycling), and electrode configuration (which are positive and which are negative) may be adjusted by the programming so as to tailor the neuromodulation of the electrodes 108 of the lead 102 to provide the best clinical outcome for the patient.

In addition, for at least one embodiment, variations of the programming may be established and programmed as well. Each implementation for a specific current and waveform may be considered as an electrode instruction set, or more simply a program, for directing the operation of the electrode 108 to achieve neuromodulation of the cavernosal nerves.

For at least one embodiment of CLRS 100, the lead 102 is an implantable lead 102, such as provided by Stim Wave, LLC, of 1310 Park Central Blvd. S, Pompano Beach, Fla. 33064, having the website stimwave.com. More specifically, for at least one embodiment the lead 102 is an adaptation of implantable neural stimulator as set forth by U.S. Pat. No. 9,199,089 to Perryman et al., and/or U.S. Pat. No. 9,220,897 Perryman et al., and/or U.S. Pat. No. 9,409,030 to Perryman et al., all incorporated herein by reference.

In addition, for at least one embodiment, the lead 102 has an attacher 150 structured and arranged to attach the lead 102 to the patient's body once implanted to minimize the chance of lead migration. For varying embodiments, this attacher 150 may be a barb, flange, spiral, coil or other element.

For at least one embodiment, CLRS 100 is provided as a kit 152, including: a removable penile control ring 104 having a flexible body formed of a resilient material enclosing: wireless communication electronics 132; a power supply 134; and control circuitry 126 associated with the wireless communication electronics 132 and power supply 134; and an implantable lead 102 having at least one electrode 108 structured and arranged to be disposed proximate to the cavernous nerve in a penis, the implantable lead 102 having the at least one electrode 108 having wireless communication electronics adapted to receive power and control from the penile control ring 104.

In varying embodiments, the kit 152 may further include one or more surgical implements for the minimally invasive procedure to implant the lead 102 proximate to the cavernous nerves of a patient.

Penile injection techniques are common for urologists who are trained in residency to place intravenous needles into the penis for various diagnostic tests, for injection of drugs into the penis, and for removal of blood from the penis. Urologists are trained to place larger implantable devices into the cavernosal bodies of the penis (penile implants).

Typical medical devices, applicable for the implantation of the lead 102 of CLRS 100 are a trocar 154—typically consisting of a cannula, also known as an introducer sheath 156 and obturator 158 which passes through the introducer sheath 156, and a guide wire 160. More generally, the trocar may be used to refer to the needle that penetrates the skin of the patient. The trocar 154 may also be structured as a finder needle, having a distal tip 162 or other section that can be stimulated during insertion to help find the desired nerve. For varying procedures, the trocar 154 maybe straight—as trocar 154A, slightly curved as trocar 154B, or even substantially curved as trocar 154C.

The introducer sheath 156 is typically plastic and is placed about the obturator 158 so that when the obturator 158 is removed the introducer sheath serves as the entry point for a guide wire 160 and/or the lead 102. To those skilled in the art, a reference of passing an item through the trocar 154 is understood and appreciated to refer to passing an item through the introducer sheath 156, whereas a reference of using the trocar 154 to identify or locate an element of anatomy or other object is appreciated to refer to the use of the obturator 158. The guide wire 160 may serve to assist the doctor in properly aligning the introducer sheath 156, and or in further identifying and confirming the location of the cavernous nerves.

Although the lead 102 may be inserted through the introducer sheath 156, for some embodiments the lead 102 may be passed over guide wire 160. This may be accomplished by selecting a lead 102 having a lumen, e.g. central cavity, appropriate to receive the guide wire 160, or by having one or more outer grooves or guides suitable to slide along or over the guide wire 160.

FIG. 2 illustrates the placement of the lead 102 in between and among elements of the cavernous nerve, with further elements of anatomy provided for ease of reference. The control ring 104 is not shown disposed about the penis for ease of illustration and discussion.

Moreover, with respect to FIG. 2 it may be appreciated that the cavernous nerve 200 runs from below the bladder 202, past and below the pubic bone 204 and into the penile organ, e.g., penis 206. Options for placement of the lead 102 therefore exist within the penis 206 alone, within the penis 206 and under the pubic bone 204, under or around the pubic bone 204 alone, at the very least.

By way of further summarization, FIG. 2 illustrates an introducer sheath 156 disposed partially into an incision 208 so as to permit introduction of the lead 102 through the introducer sheath 156 and into proximal positioning adjacent to the cavernous nerves 200. The introduction of the lead 102 by the introducer sheath 156 may be as intravenous introduction or intracavernosal introduction.

FIGS. 3A-3F conceptually illustrates at least one method of achieving cavernosal neuromodulation with an implanted lead 102 as a component of CLRS 100 as described above.

Figure 3A:
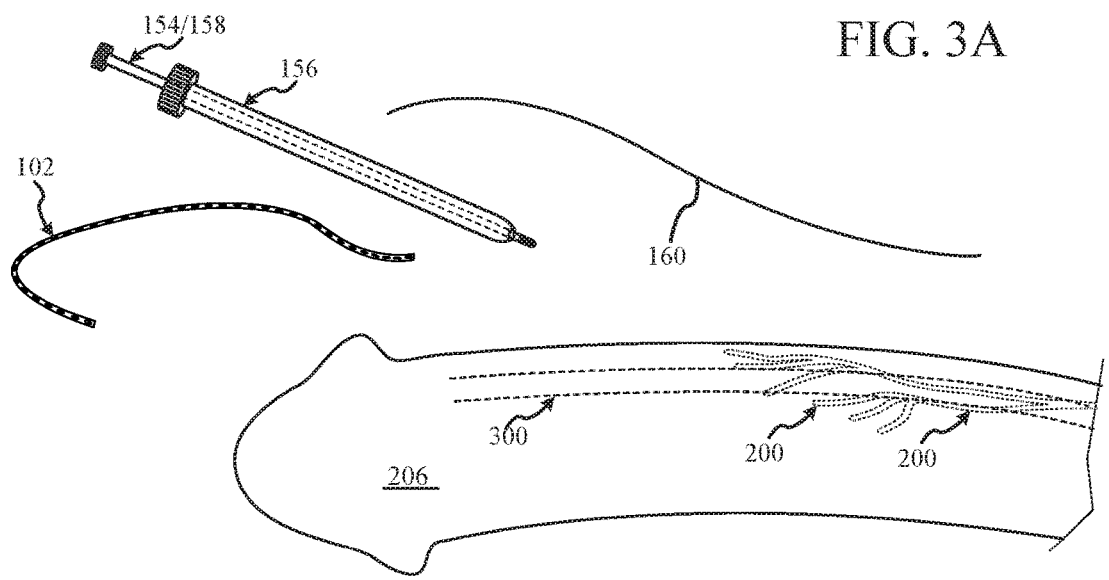
FIGS. 3A-3F illustrate a general method of implanting the implantable lead proximate to the cavernous nerves in accordance with at least one embodiment of the present invention.

In general, a practitioner will collect the basic elements of the trocar 154 having an introducer sheath 156 and obturator 158, the lead 102, and optionally a guide wire 160 as shown in FIG. 3A. As shown, the penis 206 is exposed, the anatomy of which is understood to provide options for implant in one or more veins, a cavernosa, or combinations thereof. As is shown in FIGS. 3A-3F, the cavernous nerves 200 are understood to extend from the body throughout the penis, however the cavernous nerves 200 have only been depicted proximate to the base of the penis for ease of discussion and illustration.

Figure 3B:
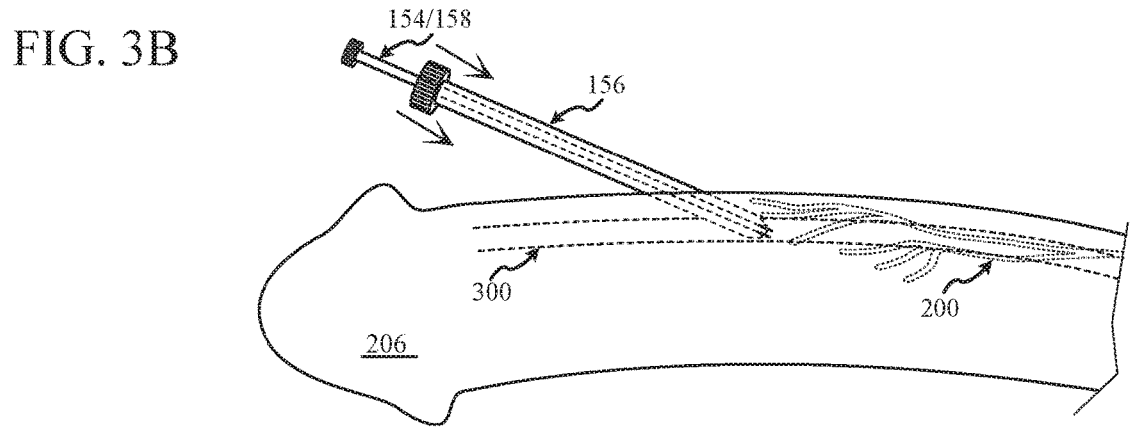
Figure 3C:
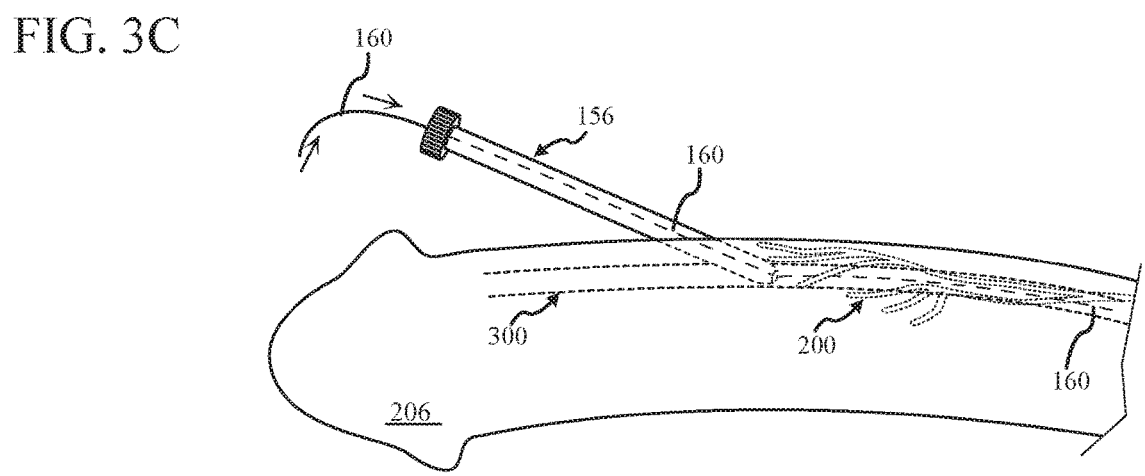

As shown in FIG. 3B the trocar 154 is used to pierce the penis and locate a cavernosa or vein—collectively referred to as passage 300. With the use of the obturator 158, or as shown in FIG. 3C, the guide wire 160, the practitioner will check to confirm the location of the cavernous nerves 200. Such determination and confirmation may be performed by selecting an obturator 158, or as shown a guide wire 160, with an eclectically active tip that may be used to trigger nerve response. Moreover, by using a metal trocar or wire with an the introducer tip the practitioner can be stimulate cavernous nerves 200 with electrical current using variable voltage or mA settings, pulse width and rate (Hz) while determining change in penile tumescence.

As the procedure is a minimally invasive procedure that may be performed as an out-patient procedure, or at the very least without full sedation and hospitalization, the procedure advantageously permits the practitioner to adapt his or her plan of implantation during the procedure. In other words, if an unsatisfactory response is received from the finder tip of the obturator or the guide wire, the practitioner may adjust course from an intravenous approach to an intracavernosal approach or vis-a-versa. Further, the practitioner may adjust from implantation within the penis alone, to implantation within the penis and proximate to the pubic bone 204 (See FIG. 2 and FIG. 7-9), or even move to implantation proximate to the pubic bone 204 alone (See FIG. 2 and FIG. 7-9).

Figure 3D:
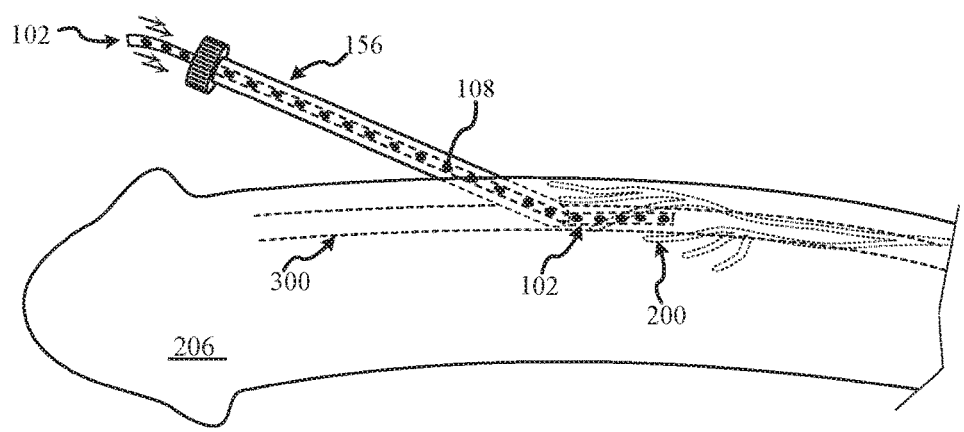

For the sake of the present example, it is presumed that good response from the cavernous nerves 200 has been determined. As such, as shown in FIG. 3D the obturator 158 has been removed, and the lead 102 is being disposed through the introducer sheath 156 and into the selected passage 300. For at least one embodiment, a blunt trocar rod may be used to further assist pushing the lead 102 into the desired position.

Figure 3E:
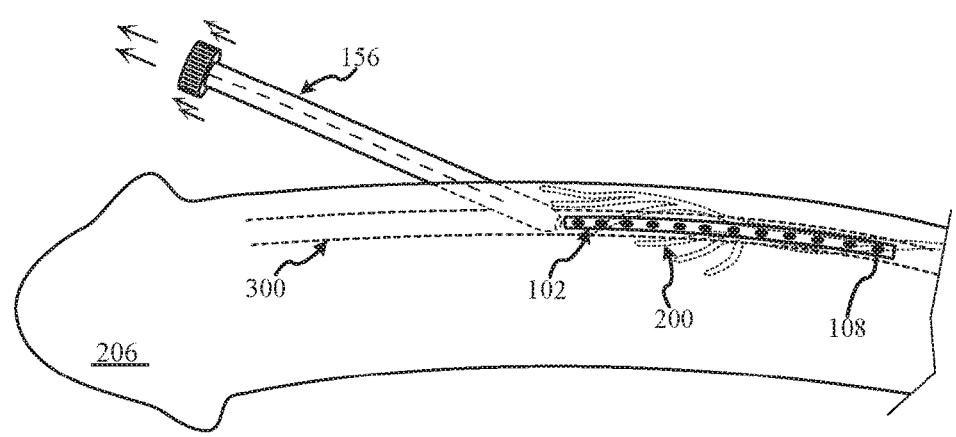

As shown in FIG. 3E, once positioned the excess portion of the lead 102 is trimmed, if such is required. Following this the trocar 154 and more specifically the introducer sheath 156 is removed and the minor incision closed by suture, glue, or other appropriate sealing means.

Figure 3F:
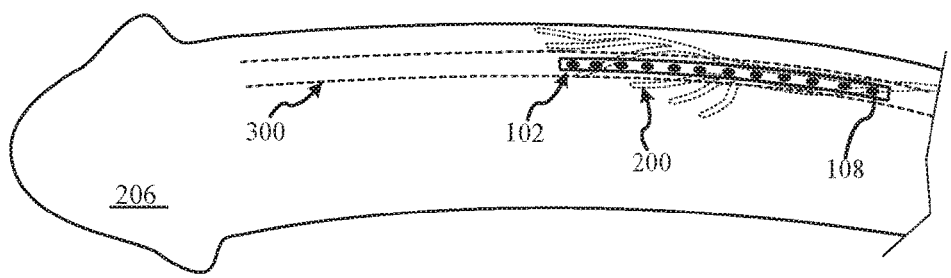

The result is as shown in FIG. 3F, the lead 102 is now disposed within the penis and the plurality of electrodes 108 are proximate to the cavernous nerves 200.

Moreover, the features and advantageous nature of CLRS 100 is stimulating the cavernous nerve 200 proximally before it separates or just after it separates. This applies to whether the lead 102 is placed via the penile or extra penile route. Further the present invention advantageously utilizes an external power source and controller, further simplifying the implant procedure. Provided as a penile control ring 104, this external power source and controller has the additional advantage of penile venous leak compression.

Having described the general nature of CLRS 100 and a general overview for how the lead 102 may be implanted, FIG. 4 presents a high-level overview for at least one method 400 for providing cavernosal neuromodulation with CLRS 100. It will be appreciated that the described method need not be performed in the order in which it is herein described, but that this description is merely exemplary of one method for providing cavernosal neuromodulation with CLRS 100.

In general, method 400 commences by implanting a lead 102 having at least one electrode 108 proximate to the cavernous nerves 200, block 402. At least four options are further depicted for how the lead 102 may be implanted. For Option A 404, method 400 progresses by piercing the penis to identify a corpora cavernosa, block 406. With the corpora cavernosa so identified, method 400 proceed with making an incision in the corpora cavernosa, block 408. Subsequently, the lead 102 is then advanced through the incision toward the cavernous nerve 200, block 410.

For Option B 412, method 400 progresses by piercing the superficial penile vein on the corpora cavernosa, block 414. Following this piercing, the lead 102 is then advanced through the incision and into the superficial penile vein and towards the cavernous nerve 200, block 416.

For Option C 418, method 400 progresses by piercing the skin using a trocar 154 based on patient anatomy, block 420. Now inserted, the trocar 154 is manipulated to advance the trocar 154 towards the proximal corpora cavernosa, block 422. Subsequently, the lead 102 is then advanced through the incision toward the cavernous nerve 200, block 424.

For Option D 426, method 400 progresses by degloving the penis to expose a corpora cavernosa, block 428. Then, the practitioner proceeds to make an incision into the corpora cavernosa, block 440. Subsequently, the lead 102 is then advanced through the incision toward the cavernous nerve 200, block 442, and the penis is re-gloved, block 444.

Following the implanting of the lead 102 by whichever method is most applicable to the patient, method 400 continues by providing the patient with an external controller and power source, such as control ring 104 as described above, block 446.

The control ring 104 is then disposed about the penis, block 448. To provide an erection, the user activates the control ring 104, and in so doing provides power to the implanted lead 102, block 440. And in response to the provided power, the electrodes 108 of the implanted lead 102 modulate and provide stimulation to the cavernous nerve 200, e.g., cavernosal neuromodulation.

To summarize, for at least one embodiment provided is a method for cavernosal neuromodulation, including: implanting at least one implantable lead 102 having at least one electrode 108 proximate to the cavernous nerve 200 in a penis 206, the at least one implantable lead 102 having the at least one electrode 108 having wireless communication electronics 118 adapted to receive power and control from an external controller; providing as an external controller a removable penile control ring 104 having a flexible body formed of a resilient material enclosing: wireless communication electronics 132; a power supply 134; and control circuitry 126 associated with the wireless communication electronics 132 and power supply 134; disposing the removable penile control ring 104 about the penis 206; and activating the control circuitry of the removable penile control ring 104 to provide at least one selected modulation to the at least one implantable lead 102 having the at least one electrode 108, thereby stimulating the cavernous nerve 200.

For all of the above lead implant options, it is specifically understood and appreciated that unlike traditional methods for cavernous nerve stimulation which include the implanting of a local power source within the subjects body and in wired communication with the implanted lead, the present invention teaches the use of an external power source and controller, which for at least one embodiment is provided as a penile ring.

Further, for all intrapenile methods described here, anatomic guidance may include bony or tissue landmarks, ultrasound and fluoroscopy (with or without intracavernosal dye) may aid in the vector to approach the proximal corpora. With the intrapenile approaches the introducer (straight or curved) with a sharp tip or blunt tip can be advanced into to the corpora cavernosa by either piercing the skin and tunica albuginea of the corpora along any portion of the penile shaft and advanced proximally toward the insertion of the cavernous nerve.

Moreover, to summarize from the above descriptions, there are at least three viable options for how the lead 102 may be implanted—intravenous implantation, intracavernosal implantation, and extra-penile implantation.

Figure 5:
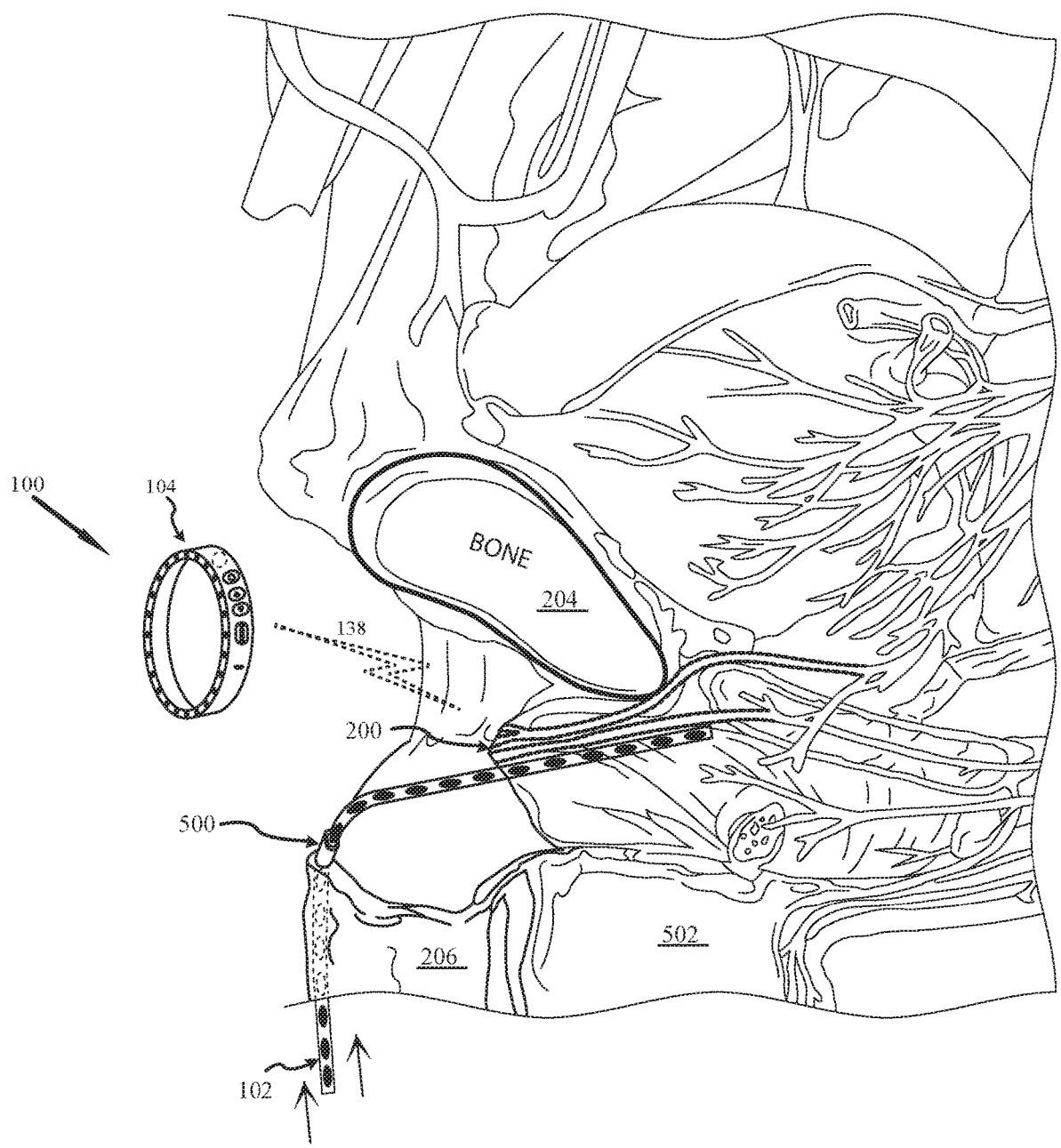
FIG. 5 is an enhanced anatomical illustration of intravenous lead placement in accordance with at least one embodiment of the present invention.

To expand from the general conceptual illustration presented in FIG. 2, FIG. 5 presents a more detailed anatomical illustration showing a partial cut away of the penis 206 and vein 500 so as to further illustrate placement of the lead 102 for intravenous lead placement extending from within the penis 206 into the body 502 and proximate to the cavernous nerves 200 below the pubic bone 204.

Moreover, the transvenous or intravenous method of lead 102 placement is via the dorsal penile vein or other superficial penile vein proximately towered the base of the penis 206, whether unilateral or bilateral, proximal or mid shaft, so as to dispose the lead 102 and more specifically the lead electrodes 108 proximate to the cavernous nerves 200 and/or it's branches.

Figure 6:
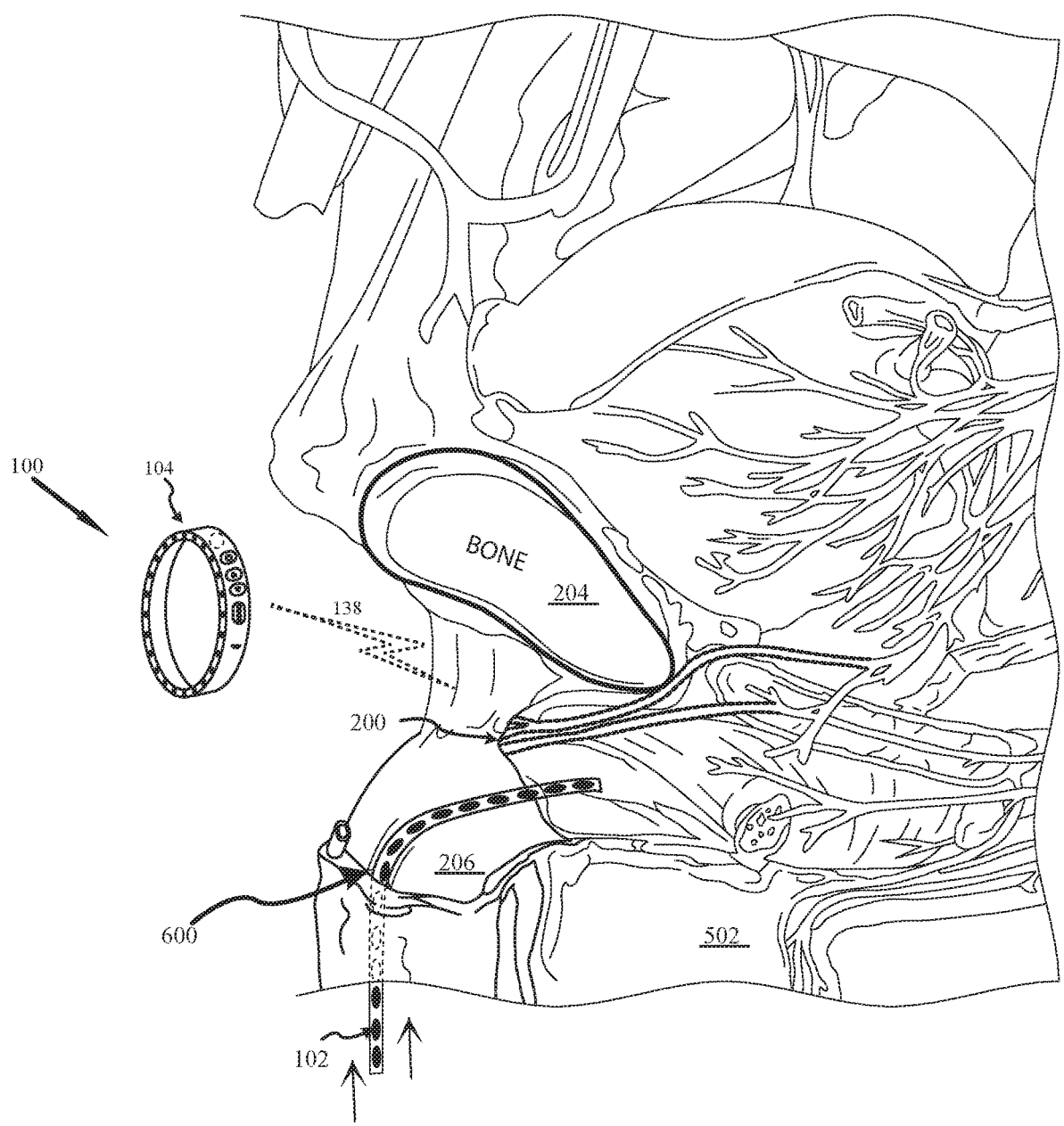
FIG. 6 is an enhanced anatomical illustration of intracavernosal lead placement in accordance with at least one embodiment of the present invention.

FIG. 6 provides a similar anatomical illustration, further depicting the relative placement of the lead 102 as disposed for intracavernosal lead placement. The intracavernosal method of lead placement involves percutaneous placement, through an introducer or needle, of the lead 102 into the corpora cavernosa 600 of the penis 206, whether unilateral or bilateral, proximal or mid shaft so as to dispose the lead 102 and more specifically the lead electrodes 108 proximate to the cavernous nerves 200 and/or its branches.

Figure 7:
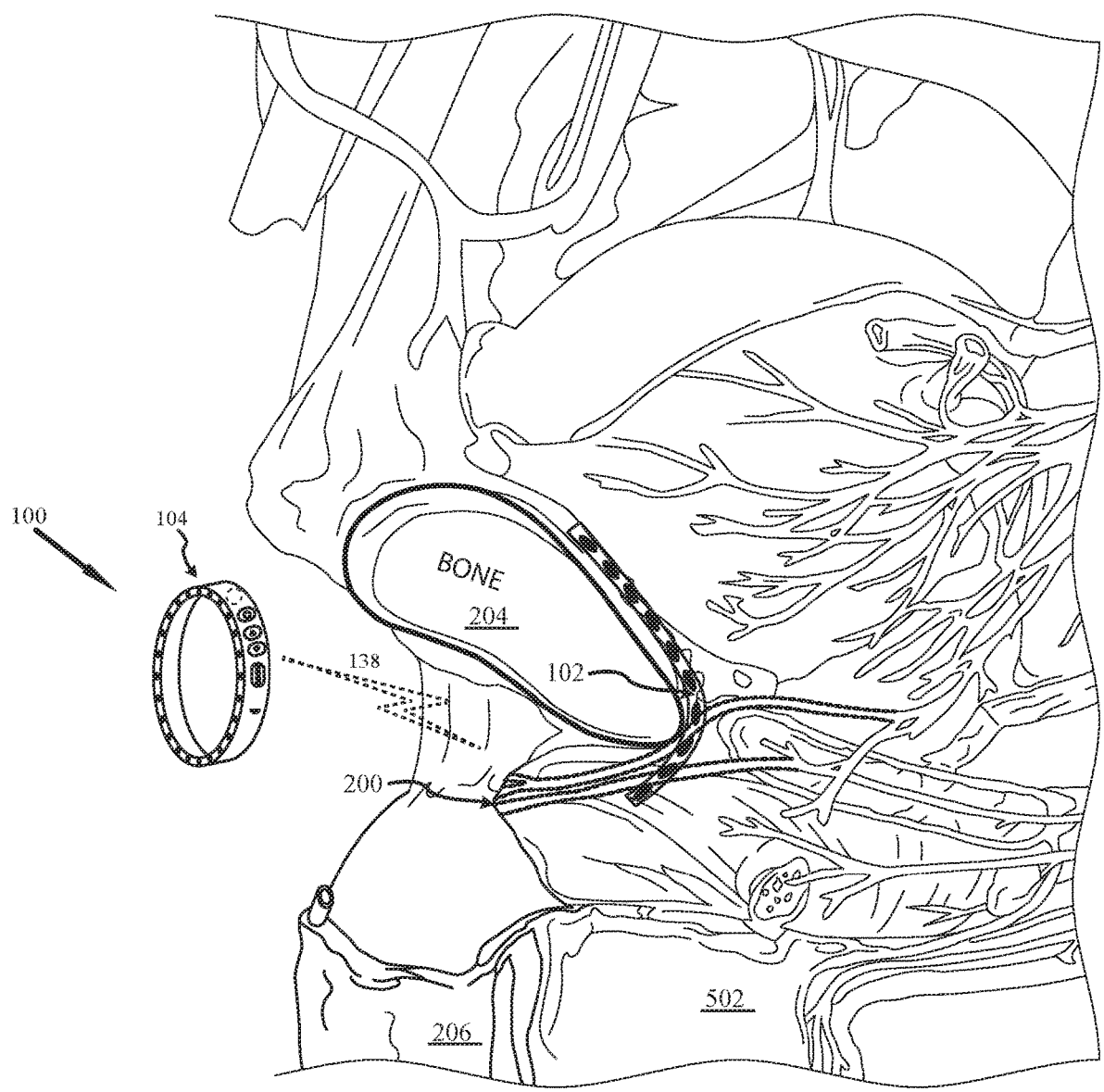
FIG. 7 is an enhanced anatomical illustration of retropubic lead placement in accordance with at least one embodiment of the present invention.
Figure 8:
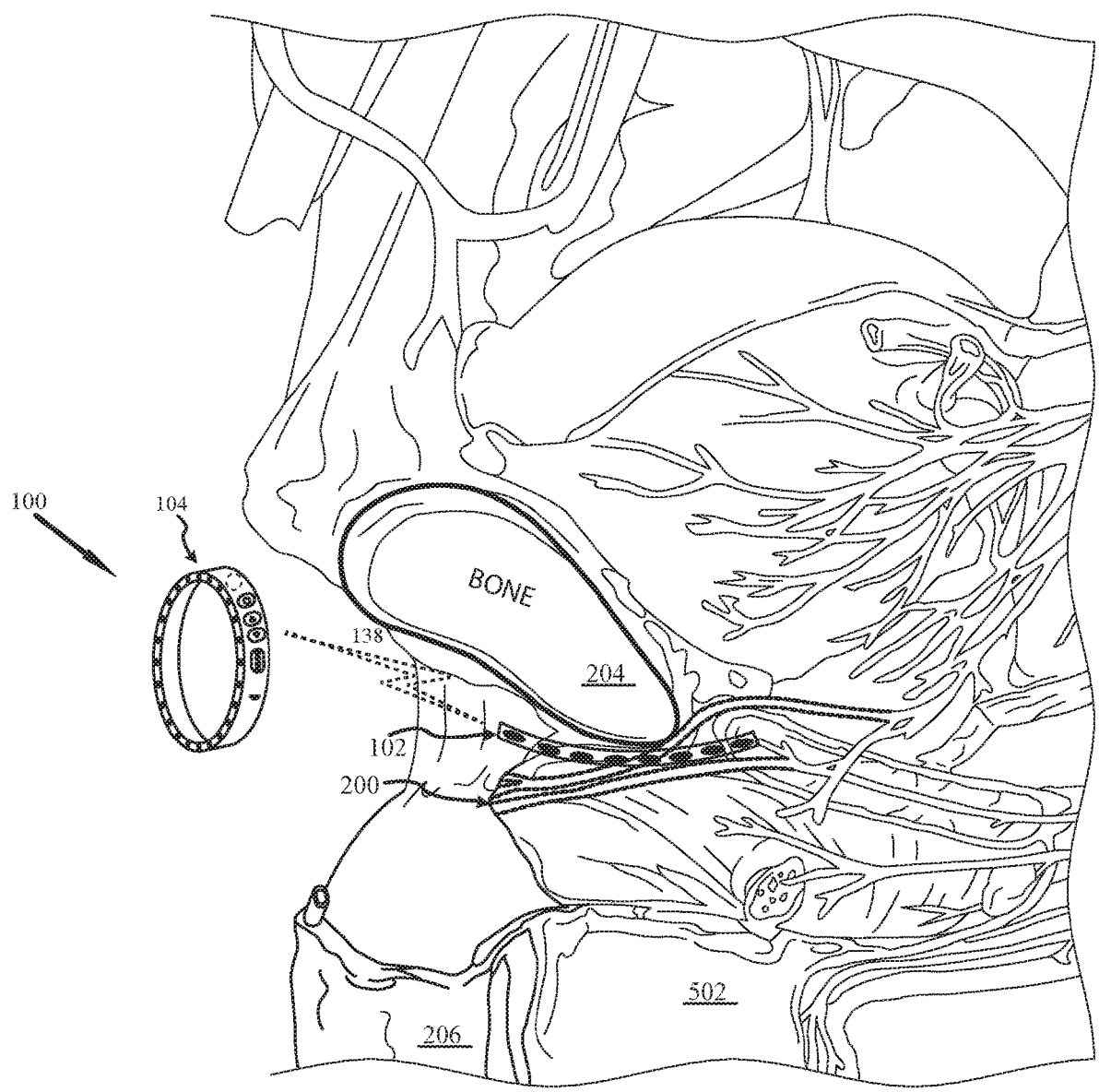
FIG. 8 is an enhanced anatomical illustration of infrapubic lead placement in accordance with at least one embodiment of the present invention.
Figure 9:
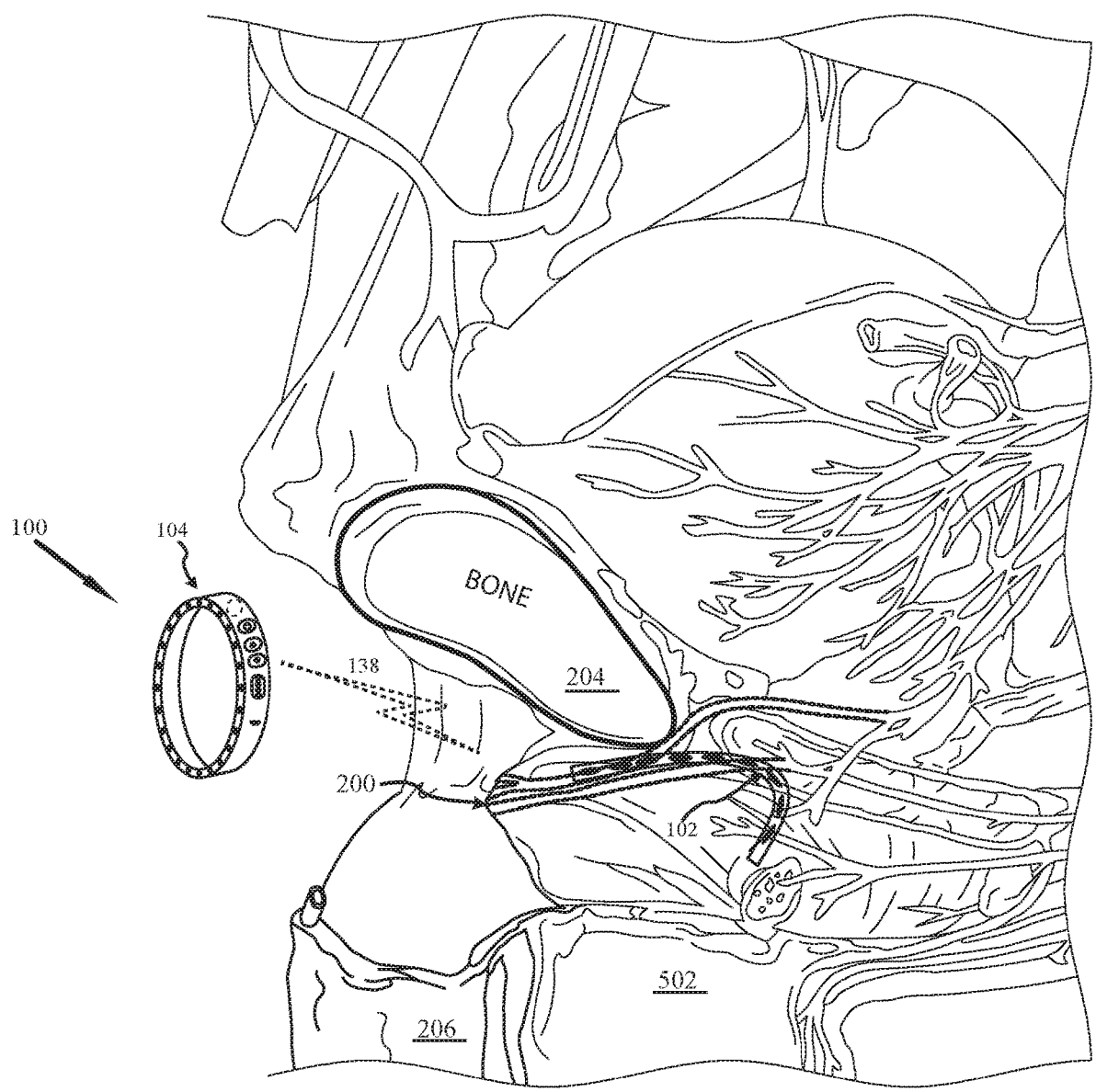
FIG. 9 is an enhanced anatomical illustration of trans obturator lead placement in accordance with at least one embodiment of the present invention.

FIGS. 7, 8 and 9 similarly present anatomical illustrations for extra-penile implantation which—FIG. 7 illustrating retropubic lead placement, wherein the pubic bone 204 serves as a reference guide during placement of the lead 102 around the pubic bone 204; FIG. 8 illustrating infrapubic lead placement, wherein the pubic bone 204 serves as a reference guide during placement of the lead 102 as guided under the pubic bone 204; and FIG. 9 illustrating trans obturator lead placement. All of the extra-penile methods are percutaneous use of a special trocar, whether straight, curved, helical or C shaped, appropriate for the patient's anatomy.

Figure 10:
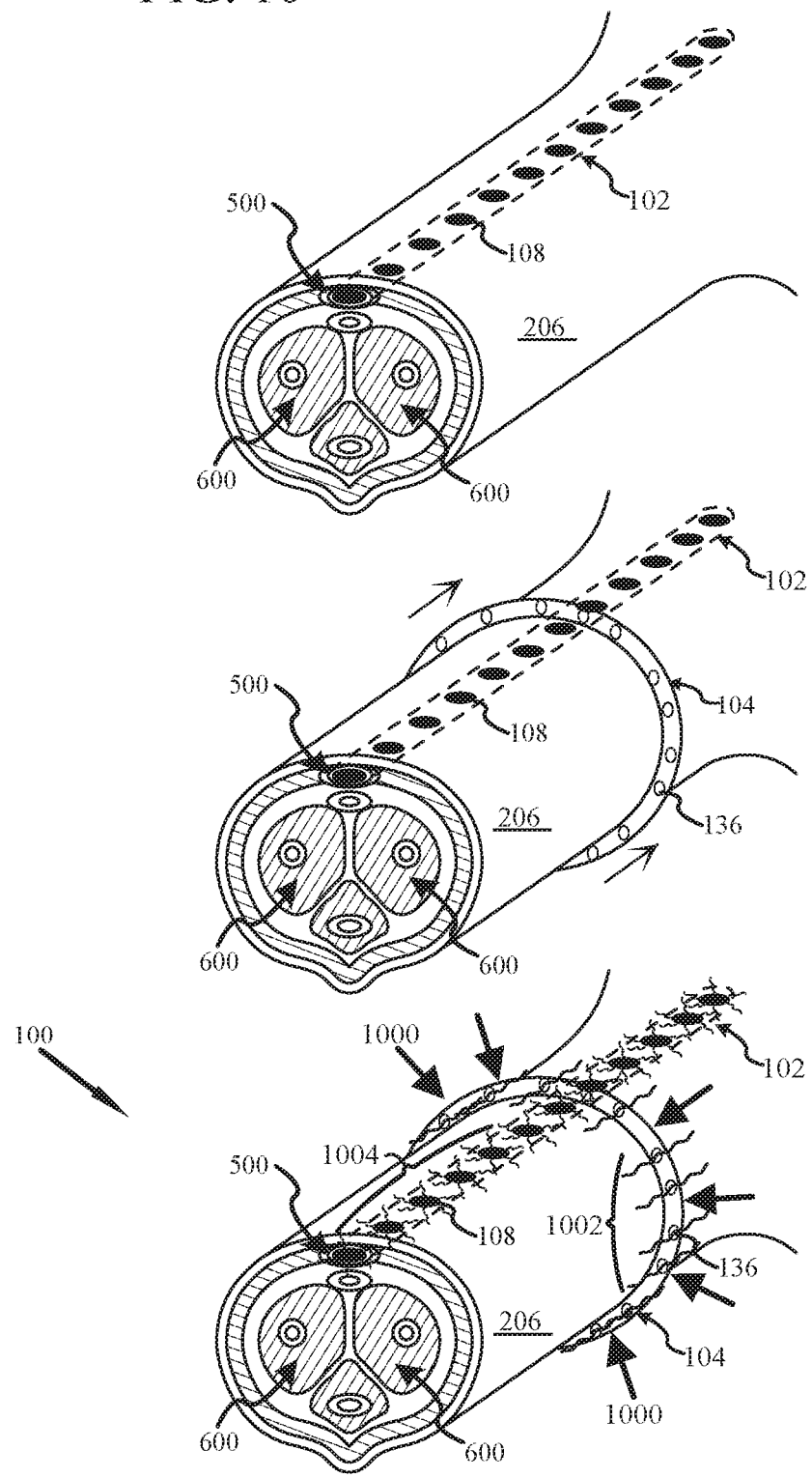
FIG. 10 is a partial cross section perspective view of a penis with an intravenous lead implant, further depicting the control ring and operation of the cavernosal lead and ring system in accordance with at least one embodiment of the present invention.
Figure 11:
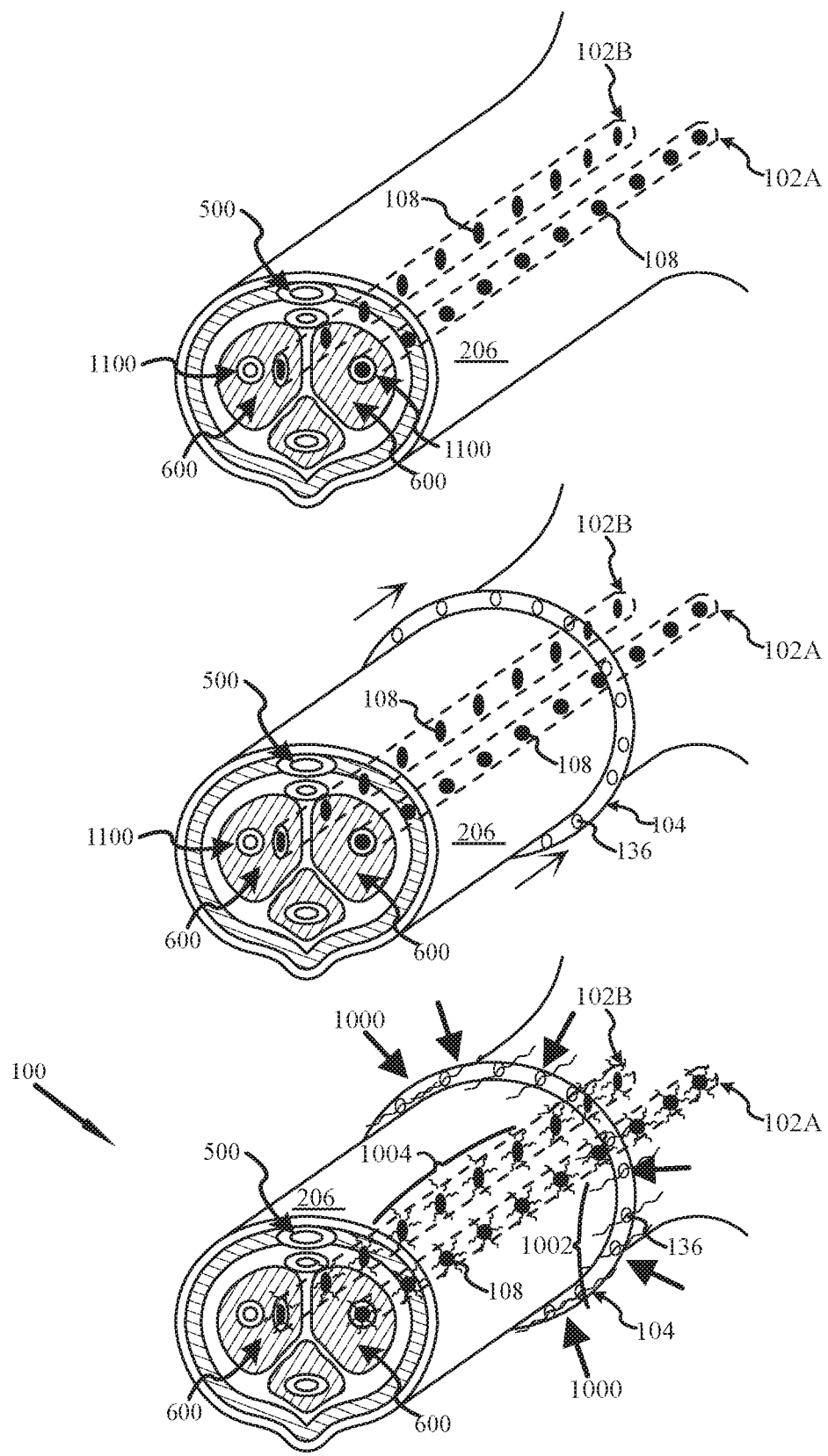
FIG. 11 is a partial cross section perspective view of a penis with an intracavernosal lead implant, further depicting the control ring and operation of the cavernosal lead and ring system in accordance with at least one embodiment of the present invention.
Figure 12:
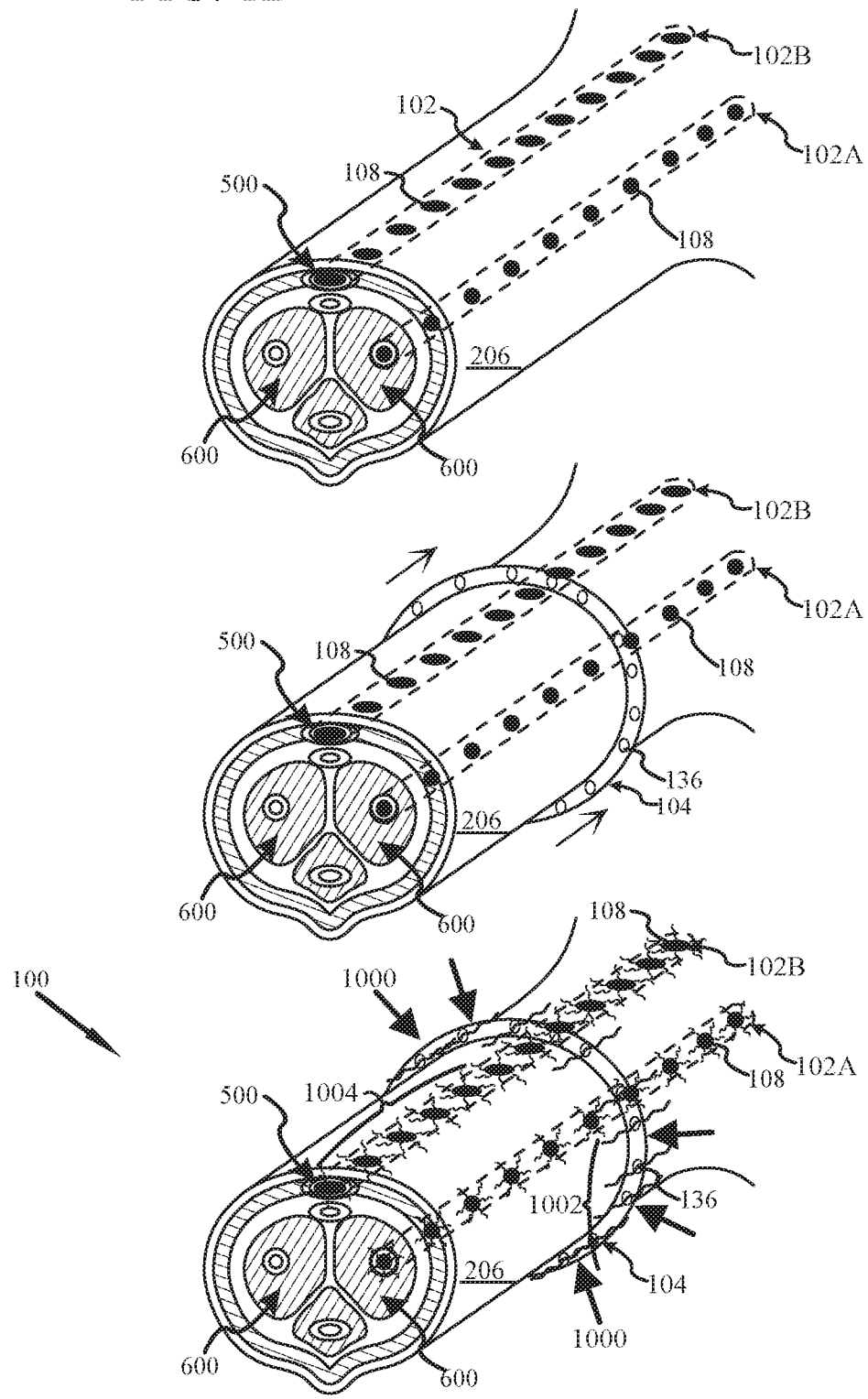
FIG. 12 is a partial cross section perspective view of a penis with an intravenous and intracavernosal lead implants, further depicting the control ring and operation of the cavernosal lead and ring system in accordance with at least one embodiment of the present invention.

FIGS. 10, 11 and 12 present partial cut away perspective views illustrating use of CLRS 100 with intravenous implantation of the lead 102 in a superficial vein 500 (FIG. 10), intracavernous implantation of the leads 102A and 102B (FIG. 11), and combined superficial intravenous and intracavernous implantation of leads 102A and 102B. From these partial cut away views, the proximate relationships of vein 500 as shown in FIG. 5 for intravenous lead placement, and the corpora cavernosa 600 as shown in FIG. 6 for intracavernosal lead placement, may be further appreciated.

With respect to FIG. 11 it is appreciated that two leads have been implanted—lead 102A being implanted within a vein within corpora cavernosa 600 and lead 102B being implanted within the corpora cavernosa 600 itself.

Moreover, for each illustration it is understood and appreciated that the lead 102 or leads 102A and 102B, have been previously implanted in accordance with one or more of the above described methods. The control ring 104 is now disposed over the penis 206 and moved to be proximate to the base of the penis 206.

The compressive nature of the control ring 104 provided constrictive force 1000 about the penis 206 so as to reduce venus leak. When the control ring 104 is activated, the antennas 136 of the control ring 104 emit energy 1002 (output signal 138) that in turn is received by the antenna(s) 114 of the implanted lead 102. The electrodes 108 of the implant lead in turn emitting electrical energy 1004 for stimulation of the cavernous nerves 200.

Moreover, it should be understood and appreciated that multiple leads 102 may be implanted in different locations and potentially used in varying combinations. Further, the relative proximity of the control ring 104 to the one or more implanted leads 102 may also be more fully appreciated.

Changes may be made in the above methods, systems and structures without departing from the scope hereof. It should thus be noted that the matter contained in the above description and/or shown in the accompanying drawings should be interpreted as illustrative and not in a limiting sense. Indeed, many other embodiments are feasible and possible, as will be evident to one of ordinary skill in the art. The claims that follow are not limited by or to the embodiments discussed herein, but are limited solely by their terms and the Doctrine of Equivalents.

What is claimed is:

1. A kit for cavernosal neuromodulation controlled and powered wirelessly from an external source, comprising:
   a removable penile control ring having a flexible body formed of a resilient material enclosing:
   wireless communication electronics;
   a power supply; and
   control circuitry associated with the wireless communication electronics and power supply; and
   an implantable lead as a unitary structure having at least one electrode structured and arranged to be disposed proximate to the cavernous nerve in a penis, the implantable lead having the at least one electrode having wireless communication electronics including an antenna with a plurality of coupling contacts adapted to receive power and control from the penile control ring to generate an electrode pulse for stimulation of the cavernous nerve when power is supplied by the penile control ring.

2. The kit for wireless cavernosal neuromodulation of claim 1, wherein the removable control ring is adjustable.

3. The kit for wireless cavernosal neuromodulation of claim 1, wherein the removable control ring provides a constriction force to the penis.

4. The kit for wireless cavernosal neuromodulation of claim 1, wherein the control ring is formed of medical grade silicon or other appropriate material.

5. The kit for wireless cavernosal neuromodulation of claim 1, wherein the at least one instruction set, pulse frequency and intensity are provided by the control circuitry of the penile control ring to the implantable lead having the at least one electrode by Bluetooth.

6. The kit for wireless cavernosal neuromodulation of claim 1, wherein the implantable lead having the at least one electrode is an implantable neural stimulator.

7. The kit for wireless cavernosal neuromodulation of claim 1, wherein power is supplied from the removable penile control ring to the implantable lead by electrical radiative coupling.

8. A method for cavernosal neuromodulation controlled and powered wirelessly from an external source, comprising:
   implanting at least one implantable lead having at least one electrode proximate to the cavernous nerve in a penis, the at least one implantable lead having the at least one electrode having wireless communication electronics including an antenna with a plurality of coupling contacts adapted to receive power and control from an external controller;
   providing as an external controller a removable penile control ring having a flexible body formed of a resilient material enclosing:
   wireless communication electronics;
   a power supply; and
   control circuitry associated with the wireless communication electronics and power supply;
   disposing the removable penile control ring about the penis; and
   activating the control circuitry of the removable penile control ring to provide at least one selected instruction set to the at least one implantable lead having the at least one electrode to generate an electrode pulse with power as supplied by the penile control ring, thereby stimulating the cavernous nerve.

9. The method of claim 8, wherein the portable power supply and controller are integrated in a removable control ring structured and arranged to be disposed about the penis, power provided to the electrode by electrical radiative coupling.

10. The method of claim 8, wherein the removable control ring is adjustable.

11. The method of claim 8, wherein the removable control ring provides a constriction force to the penis.

12. The method of claim 8, wherein the control ring is formed of medical grade silicon.

13. The method of claim 8, wherein the at least one instruction set, pulse frequency and intensity are provided by the controller to the at least one implantable lead having the at least one electrode by Bluetooth.

14. The method of claim 8, wherein the implanting of the at least one implantable lead having the at least one electrode is performed by:
   piercing the penis to identify a corpora cavernosa;
   making an incision in the corpora cavernosa; and
   advancing the at least one implantable lead having the at least one electrode through the incision towards the cavernous nerve.

15. The method of claim 8, wherein the implanting of the at least one implantable lead having the at least one electrode is performed by:
   piercing the superficial penile vein on the corpora cavernosa; and
   advancing the at least one implantable lead having the at least one electrode through the piercing towards the cavernous nerve.

16. The method of claim 8, wherein the implanting of the at least one implantable lead having the at least one electrode is performed by:
   piercing the skin using a special trocar based on patient anatomy;
   passing a trocar towards the proximal corpora cavernosa; and
   advancing the at least one implantable lead having the at least one electrode through the trocar towards the cavernous nerve.

17. The method of claim 8, wherein the implanting of the at least one implantable lead having the at least one electrode is performed by:
   degloving the penis to expose a corpora cavernosa;
   making an incision in the corpora cavernosa;
   advancing the at least one implantable lead having the at least one electrode through the incision towards the cavernous nerve; and
   re-gloving the penis.

18. The method of claim 8, wherein the implanting of the at least one implantable lead having the at least one electrode is performed by:
  making an incision in the penis skin;
  making an incision in the corpora cavernosa; and
  advancing the at least one implantable lead having the at least one electrode through the incision towards the cavernous nerve.

19. The method of claim 8, wherein power is supplied from the removable penile control ring to the implantable lead by electrical radiative coupling.

* * * * *